United States Patent
Nakamura et al.

(10) Patent No.: US 9,772,316 B2
(45) Date of Patent: Sep. 26, 2017

(54) OXYGEN DETECTING AGENT COMPOSITION, AND MOLDED ARTICLE, SHEET, PACKAGING MATERIAL FOR OXYGEN SCAVENGER, AND OXYGEN SCAVENGER USING THE SAME

(71) Applicant: MITSUBISHI GAS CHEMICAL COMPANY, INC., Tokyo (JP)

(72) Inventors: Kazuhiro Nakamura, Tokyo (JP); Hiroki Saito, Tokyo (JP); Ken Sugito, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/025,914

(22) PCT Filed: Oct. 6, 2014

(86) PCT No.: PCT/JP2014/076685
§ 371 (c)(1),
(2) Date: Mar. 30, 2016

(87) PCT Pub. No.: WO2015/050270
PCT Pub. Date: Apr. 9, 2015

(65) Prior Publication Data
US 2016/0216243 A1   Jul. 28, 2016

(30) Foreign Application Priority Data

Oct. 4, 2013 (JP) ................................ 2013-209349
Jan. 24, 2014 (JP) ................................ 2014-011244

(51) Int. Cl.
*G01N 31/22* (2006.01)
*G01N 21/78* (2006.01)
*B65D 81/26* (2006.01)

(52) U.S. Cl.
CPC .......... *G01N 31/225* (2013.01); *B65D 81/266* (2013.01); *G01N 21/783* (2013.01)

(58) Field of Classification Search
CPC ... G01N 27/783; G01N 31/225; B65D 81/266
See application file for complete search history.

(56) References Cited

U.S. PATENT DOCUMENTS

| | | | |
|---|---|---|---|
| 5,310,497 A * | 5/1994 | Ve Speer | A23L 3/3436 206/524.2 |
| 6,093,572 A | 7/2000 | Stenholm et al. | |
| 6,399,387 B1 | 6/2002 | Stenholm et al. | |
| 6,627,443 B1 | 9/2003 | Stenholm et al. | |
| 2008/0300133 A1 | 12/2008 | Langowski et al. | |
| 2011/0136238 A1 * | 6/2011 | Hurme | B65D 79/02 436/1 |

FOREIGN PATENT DOCUMENTS

| | | |
|---|---|---|
| GB | 1564467 | 9/1977 |
| GB | 2298273 | 8/1996 |
| JP | 60-131459 | 7/1985 |
| JP | 3-205560 | 9/1991 |
| JP | 2000-515246 | 11/2000 |
| JP | 2004-45365 | 2/2004 |
| JP | 2007-298315 | 11/2007 |
| JP | 2008-96375 | 4/2008 |
| JP | 2009-516836 | 4/2009 |
| WO | 94-17199 | 8/1994 |
| WO | 98/03866 | 1/1998 |
| WO | 2005/088298 | 9/2005 |

OTHER PUBLICATIONS

Meeussen, Johannes C. L. et al. "Dissolution behavior of iron cyanide (Prussian blue) in contaminated soils." Environ. Sci. Technol. (1992) 26 1832-1838.*
Samain, Louise et al. "Relationship between the synthesis of Prussian blue pigments, their color, physical properties, and their behavior in paint layers." J. Phys. Chem. C (2013) 117 9693-9712.*
Ware, Mike. "Prussian blue: Artists' pigment and chemists' sponge." J. Chem. Ed. (2008) 85 612-621.*
International Search Report issued in Patent Application No. PCT/JP2014/076685, dated Jan. 13, 2015, and English version.
International Preliminary Report on Patentability issued in Patent Application No. PCT/JP2014/076685, dated Apr. 5, 2016, and English version.

* cited by examiner

*Primary Examiner* — Christopher A Hixson
(74) *Attorney, Agent, or Firm* — Greenblum & Bernstein, P.L.C.

(57) ABSTRACT

Provided is an oxygen detecting agent composition including a redox dye and a reducing agent, the redox dye being an inorganic substance.

9 Claims, No Drawings

OXYGEN DETECTING AGENT COMPOSITION, AND MOLDED ARTICLE, SHEET, PACKAGING MATERIAL FOR OXYGEN SCAVENGER, AND OXYGEN SCAVENGER USING THE SAME

TECHNICAL FIELD

The present invention relates to an oxygen detecting agent composition, and a molded article, a sheet, a packaging material for an oxygen scavenger and an oxygen scavenger using the same.

BACKGROUND ART

There have hitherto been proposed oxygen detecting agents using organic dyes which undergo reversible color change due to oxidation and reduction. Commercially available oxygen detecting agents (for example, trade name "Ageless Eye," manufactured by Mitsubishi Gas Chemical Company, Inc.) are function products simply showing by color change that the oxygen concentration in a transparent packaging container is in a deoxygenated state of less than 0.1% by volume, and are used together with oxygen scavengers for food freshness maintenance, quality maintenance of medical pharmaceuticals and the like. Many of conventional oxygen detecting agents allow the presence or absence of oxygen in a system to be visually identifiable by using a redox dye in combination with an appropriate reducing agent.

In conventional oxygen detecting agents, organic dyes typified by methylene blue are used as redox dyes, and these organic dyes sometimes cause transfer to and contamination of, for example, packaging materials. In this regard, for example, Patent Literature 1 proposes an oxygen indicator in which an oxygen detecting agent composition containing methylene blue and a cyclic olefin copolymer are laminated on each other. Patent Literature 2 proposes an oxygen detecting agent composition in which methylene blue is impregnated into a layered silicate.

CITATION LIST

Patent Literature

Patent Literature 1: Japanese Patent Laid-Open No. 2008-096375
Patent Literature 2: Japanese Patent Laid-Open No. 2004-045365

SUMMARY OF INVENTION

Technical Problem

However, the oxygen detecting agent composition of Patent Literature 1 or the Patent Literature 2 uses an organic dye as a redox dye, and accordingly, suffers from a problem that when the oxygen detecting agent composition is exposed to a high-temperature atmosphere, for example, in a heat sterilization treatment, the organic dye is eluted to contaminate the packaging material or the like. Accordingly, the color of the oxygen detecting agent is sometimes misidentified, or the beauty of the exterior appearance of the packaging material or the like is sometimes impaired.

The present invention has been made in view of the above-described circumstances, and takes as its object the provision of an oxygen detecting agent composition capable of preventing the elution of the redox dye even when the oxygen detecting agent composition is exposed to a high-temperature atmosphere, for example, in a heat sterilization treatment.

Solution to Problem

The present inventors investigated the method for solving the above-described problems, and have perfected the present invention by discovering that by using an inorganic substance as a redox dye, the elution of the redox dye can be suppressed even when the oxygen detecting agent composition is exposed to a high-temperature atmosphere.

Specifically, the present invention is as follows.

<1> An oxygen detecting agent composition including a redox dye and a reducing agent, wherein the redox dye is an inorganic substance.

<2> The oxygen detecting agent composition according to <1>, wherein a solubility of the redox dye in water at 20° C. is 1 mg/100 g-$H_2O$ or less.

<3> The oxygen detecting agent composition according to <1> or <2>, wherein the redox dye is an iron blue pigment.

<4> The oxygen detecting agent composition according to any one of <1> to <3>, further including a basic substance.

<5> The oxygen detecting agent composition according to any one of <1> to <4>, further including a sodium salt and/or sodium ion.

<6> The oxygen detecting agent composition according to any one of <1> to <5>, further including a support.

<7> A molded article including the oxygen detecting agent composition according to any one of <1> to <6>.

<8> A sheet including the oxygen detecting agent composition according to any one of <1> to <6>.

<9> A packaging material for an oxygen scavenger, including the molded article according to <7>, or the sheet according to <8>.

<10> An oxygen scavenger including an oxygen scavenger composition, and the packaging material for an oxygen scavenger according to <8> which packages the oxygen scavenger composition.

Advantageous Effects of Invention

According to the present invention, it is possible to provide an oxygen detecting agent composition capable of suppressing the elution of the redox dye even when the oxygen detecting agent composition is exposed to a high-temperature atmosphere.

DESCRIPTION OF EMBODIMENTS

Hereinafter, the embodiment for carrying out the present invention (hereinafter, simply referred to as "the present embodiment") is described in detail. The following present embodiment is presented as exemplification for describing the present invention, and the present invention is not intended to be limited only to the following contents. The present invention can be carried out as appropriately modified within the scope of the gist of the present invention.

The oxygen detecting agent composition of the present embodiment includes a redox dye and a reducing agent, wherein the oxygen detecting agent composition is an inorganic substance. The use of the redox dye, which is an inorganic substance, in combination with the reducing agent allows the elution of the redox dye to be suppressed even in a high-temperature atmosphere.

<Redox Dye>

The redox dye means a substance which undergoes a reversible color change between the oxidized state and the reduced state thereof. The redox dye of the present embodiment is not particularly limited as long as the redox dye is an inorganic substance; however, a Prussian blue-type complex is preferable, and an iron blue pigment is more preferable. The inorganic substance as referred to herein means a substance having no C—C bond(s) and no C—H bond(s) in the molecular structure thereof.

Examples of the Prussian blue-type complex include the substances containing compound (1) represented by the following general formula (1); however, the Prussian blue-type complex can take various forms as described later.

$$A_xMA[MB(CN)_6]_y\cdot zH_2O \quad (1)$$

(wherein A represents a cation; MA represents a metal atom(s) of one or two or more types of metals selected from the group consisting of vanadium, chromium, manganese, iron, ruthenium, cobalt, rhodium, nickel, palladium, platinum, copper, silver, zinc, lanthanum, europium, gadolinium, lutetium, barium, strontium and calcium; MB represents a metal atom(s) of one or two or more types of metals selected from the group consisting of vanadium, chromium, molybdenum, tungsten, manganese, iron, ruthenium, cobalt, nickel, platinum and copper; x is a number of 0 to 3, y is a number of 0.3 to 1.5; and z is a number of 0 to 30.)

In the general formula (1), the cyano groups (CN) may be partially substituted with a hydroxyl group, an amino group, a nitro group, a nitroso group, water and the like. The compound (1) is not necessarily required to contain the cation A (for example, see the case of x=0). When the compound (1) contains the cation A, examples of the cation A include, without being limited to: cations of potassium, sodium, cesium, rubidium, hydrogen, and $NH_4$. The compound (1) may also further contain other components such as anions. The compound (1) is not necessarily required to contain water (for example, see the case of z=0). Any Prussian blue-type complex which contains the compound (1) can be used, and the Prussian blue-type complex may contain a complex having another structure.

The iron blue pigment contains a compound in which in the general formula (1), the cation A is one or two or more types of the cations of the components selected from the group consisting of $NH_4$, K, Na and Fe(II), MA is Fe(III), and MB is Fe(II). The redox dye is preferably an iron blue pigment in the oxygen detecting agent composition of the present embodiment. In the present specification, when A is the cation of $NH_4$, the iron blue pigment is referred to as ammonium iron blue pigment; when A is the cation of K, the iron blue pigment is referred to as potassium iron blue pigment; when A is the cation of Na, the iron blue pigment is referred to as sodium iron blue pigment; and when A is the cation of Fe(II), the iron blue pigment is referred to as iron hexacyanoferrate (iron(III) hexacyanoferrate(II)).

Specifically, the iron blue pigment can also be referred to as the compound represented by the following general formula (1a):

$$MFe(III)[Fe(II)(CN)_6] \quad (1a)$$

(wherein M represents $NH_4$, K, Na, or Fe(II).)

The above-described redox dyes may be used each alone or in combinations of two or more thereof. These redox dyes may also contain crystallization water. Moreover, in the general formula (1), A, Fe(III), or Fe(II) may be partially substituted with another metal, or Fe(II) may be partially deficient. As the iron blue pigment, commercially available products can also be used. The commercially available products are commercially available under the names of, for example, Prussian blue, Milori blue, Paris blue, and Chinese blue.

The redox dye is preferably low in the solubility in water; specifically, the solubility in water at 20° C. is preferably 1 mg/100 g-$H_2O$ or less, more preferably 0.1 mg/100 g-$H_2O$ or less, and furthermore preferably 0.01 mg/100 g-$H_2O$ or less. The lower the solubility in water of the redox dye is, the more effectively the contamination risk due to the elution of the dye can be reduced.

From the viewpoint of chemical stability or improvement of dispersibility in a solvent, it is possible to use a redox dye subjected to surface hydrophobization treatment with, for example, an alkyl group or silicone to an extent not to disturb the color change reaction. The primary particle size of the redox dye is preferably 1 to 500 nm and more preferably 50 to 100 nm in the average particle size. The average particle size as referred to herein means the number average particle size determined by dynamic light scattering.

<Reducing Agent>

The reducing agent is not particularly limited as long as the reducing agent is a compound capable of reducing the redox dye in the oxidized state thereof, and heretofore known reducing agents can be used as the reducing agent. Examples of the reducing agent include: monosaccharides such as glucose, fructose and xylose; disaccharides such as maltose; ascorbic acid and the salts thereof; dithionous acid and the salts thereof; and cysteine and the salts thereof. These may be used each alone or in combinations of two or more thereof. Among these, from the viewpoint of the resistance to heat sterilization treatment and stability, monosaccharides or disaccharides are preferable, and disaccharides are more preferable, and maltose is furthermore preferable.

The content of the reducing agent in the oxygen detecting agent composition of the present embodiment is not particularly limited; however, from the viewpoint of the reduction capability or the like, the content of the reducing agent is preferably equivalent or more based on the redox dye, in terms of the molar ratio. When the redox dye is an iron blue pigment, the content of the reducing agent is preferably the amount equal to or higher than the amount capable of converting all the oxidized type of the iron blue pigment into the reduced type; without being particularly limited, usually, the amount of the reducing agent is preferably 2 to 100 times, more preferably 3 to 50 times and furthermore preferably 5 to 30 times, as large as the amount of the iron blue pigment in terms of mass.

<Sodium Salt and Sodium Ion>

The oxygen detecting agent composition of the present embodiment preferably includes a sodium salt and/or sodium ion. The presence of a sodium salt and/or sodium ion in the oxygen detecting agent composition allows the elution of the redox dye (dye contamination) to be suppressed even in a high temperature-high humidity atmosphere in a heat sterilization treatment or the like, and also allows the redox dye to change the color thereof as a result of rapid response to the oxygen concentration change so as to further improve the oxygen detection performance. In particular, when the redox dye included in the oxygen detecting agent composition is an iron blue pigment, the above-described effect is more remarkable. Even when the oxygen detecting agent composition is exposed to a high temperature treatment such as a heat sterilization treatment, the oxygen detecting agent composition can suppress the elution of the redox dye, and has an excellent oxygen detection performance, and accordingly, it is expected that, for example, the oxygen detecting agent composition more facilitates the detection of pin holes in an oxygen barrier bag, and thus, it can more save labor in the detection and exclusion of defective products.

Examples of the sodium salt include: inorganic salts such as sodium chloride, sodium nitrate, and sodium phosphate; and organic acid salts such as sodium acetate, sodium tartrate, sodium citrate and sodium malate. Among these, organic acid salts are preferable, sodium salts of polybasic acids such as sodium phosphate, sodium sulfate, and sodium citrate are more preferable, and sodium citrate is furthermore preferable. The sodium salt may be included as solid or in a state of being dissolved in a solvent such as water or alcohol, in the oxygen detecting agent composition. In the present embodiment, either the state of being a sodium salt or the state of being sodium ion may be adopted. These sodium salts and sodium ion may be used each alone or in combinations of two or more thereof.

The sodium ion may be the sodium ion generated from the material generating sodium ion in the system. Examples of such sodium ion include: the sodium ions generated from the sodium contained in sodium iron blue pigment, sodium contained in the reducing agent such as sodium ascorbate, sodium contained in a support, and sodium contained in a fibrous base material. Alternatively, examples of such sodium ion also include: the sodium ion generated from a fibrous material (such as paper) containing as a binder, for example, a sodium salt of a polymer such as sodium polyacrylate.

The behavior of the sodium salt and the sodium ion in the case where the redox dye is a Prussian blue-type complex can take various modes. Examples of such a mode include: the mode of being incorporated into the crystal lattice of the complex; the mode of being released from the crystal lattice of the complex to form a salt with an anion in the composition; and the mode of being present in a state of being isolated as ion. The number of the ions incorporated into the complex can be one or more (the mode in the present embodiment is not limited to these).

The total amount of the contents of the sodium salt and the sodium ion in the oxygen detecting agent composition of the present embodiment is not particularly limited; however, the total amount is preferably 0.01 to 10 times, preferably 0.05 to 2 times, further preferably 0.05 to 1.5 times, furthermore preferably 0.1 to 1.5 times and still furthermore preferably 0.1 to 1.1 times, as large as the content of the redox dye, in terms of the mass of the sodium atom. By regulating the total amount of the contents of the sodium salt and the sodium ion so as to fall within the above-described range, the oxygen detection speed can be more improved. The reason for this is not clear at present, but it is inferred that this is because the incorporation of the sodium ion into the crystal lattice of the Prussian blue-type complex changes the oxidation-reduction potentials of the metal ions constituting the complex. It is inferred that among the various metal ions, the incorporation of the sodium ion into the metal complex tends to favorably affect the oxidation-reduction potentials, and consequently, the oxygen detection performance in rapidly changing the color with the oxygen concentration change is more improved (however, the mechanism of the present embodiment is not limited to this).

<Basic Substance>

From the viewpoint of enhancing the reduction activity of the reducing agent, the oxygen detecting agent composition of the present embodiment preferably further includes a basic substance. Examples of the basic substance include: alkali metal hydroxides such as sodium hydroxide and potassium hydroxide; alkali-earth metal hydroxides such as calcium hydroxide; alkali metal carbonates such as sodium carbonate and potassium carbonate; alkali metal hydrogencarbonates such as sodium hydrogencarbonate; and alkali metal phosphates such as tripotassium phosphate. Among these, the alkali-earth metal hydroxides and the alkali-earth metal carbonates are preferable, and the alkali-earth metal carbonates are more preferable.

The content of the basic substance in the oxygen detecting agent composition of the present embodiment is preferably 10 to 1000 times, more preferably 50 to 500 times, further preferably 100 to 300 times, and furthermore preferably 100 to 200 times, as large as the content of the redox dye, in terms of mass. By regulating the content of the basic substance so as to fall within the above-described range, it is possible to more enhance the storage stability and the color response speed against the oxygen concentration.

<Moisturizing Agent>

From the viewpoint of holding the moisture necessary for the color change reaction, the oxygen detecting agent composition of the present embodiment can further include a moisturizing agent. Examples of the moisturizing agent include: polyhydric alcohols such as ethylene glycol, glycerin and polyethylene glycol; and hygroscopic inorganic salts such as magnesium sulfate, magnesium chloride and calcium chloride.

The content of the moisturizing agent in the oxygen detecting agent composition of the present embodiment is preferably 1 to 20% by mass and more preferably 5 to 15% by mass, based on the total amount of the oxygen detecting agent composition. The content of the moisturizing agent regulated to fall within the above-described range allows the normal coloration function to be provided over a wider atmospheric humidity range.

<Colorant>

In the present embodiment, the color change of the redox dye can be made clear by adding a colorant which does not change the color thereof depending on the oxygen concentration and does not cause contamination during heat sterilization treatment. Examples of such a colorant include, without being limited to: dyes such as Red No. 104 and Acid Red; and pigments such as titanium oxide and red iron oxide.

The content of the colorant is not particularly limited as long as the color change of the redox dye can be visually identified; however, the content of the colorant is preferably 0.01 to 5% by mass, more preferably 0.05 to 3% by mass and furthermore preferably 0.1 to 1% by mass, based on the total amount of the oxygen detecting agent composition. When the redox dye is an iron blue pigment, the content of the colorant is preferably 0.0001 to 5% by mass, more preferably 0.01 to 5% by mass, furthermore preferably 0.01 to 3% by mass, and still furthermore preferably 0.03 to 1% by mass, based on the total amount of the oxygen detecting agent composition.

<Support>

When the oxygen detecting agent composition of the present embodiment is in a powder form, and the handleability of such composition is intended to be improved, the oxygen detecting agent composition preferably further includes a support. By allowing the respective components in the oxygen detecting agent composition to be supported on the support, the handleability of the oxygen detecting agent composition can be improved while the composition being in a powder form. The particle size of the oxygen detecting agent in a powder form is not particularly limited; however, from the viewpoint of the fluidity, the particle size of the oxygen detecting agent in a powder form is preferably 10 to 1000 μm and more preferably 50 to 500 μm. The average particle size as referred to herein means the particle size as measured from the weight fractions determined by the sizes of the sieve openings after vibrating the particles for 5 minutes in different sieves wherein the standard sieves of JIS Z 8801 are used.

Examples of the support include: inorganic substances such as magnesium carbonate, zeolite, diatom earth, perlite, activated alumina and silica gel. Among these, from the viewpoint of the color responsivity to oxygen, the support is preferably a basic inorganic substance, and more preferably magnesium carbonate. When the support is a basic inorganic substance, the support can also provide the function as the above-described basic substance.

<Oxygen Detecting Agent Ink>

The oxygen detecting agent composition of the present embodiment is, if necessary, dispersed in a solvent together with a binder, and thus an oxygen detecting agent ink (sometimes, also referred to as an "oxygen indicator ink" or the like) can be prepared.

<Solvent>

The solvent can be used by selecting, in consideration of the solubility and dispersibility of the oxygen detecting agent composition, the compatibility with the printing method and the like. Examples thereof include water; alcohols such as isopropanol and butanol; esters such as ethyl acetate and butyl acetate; ketones such as methyl ethyl ketone and methyl isobutyl ketone; and hydrocarbons such as toluene and cyclohexane. These may be used each alone or in combinations of two or more thereof.

<Binder>

Examples of the binder include: water-soluble polymers such as sodium alginate, gum arabic, tragacanth gum, carboxymethyl cellulose, hydroxyethyl cellulose, methylcellulose, dextrin, polyvinyl alcohol, sodium polyacrylate and polyacrylamide; celluloses such as ethyl cellulose, ethylhydroxyethyl cellulose and cellulose acetyl propionate; and water-insoluble polymers such as vinyl acetate resin, butyral resin, polyester resin, acrylic resin, polyether resin, polyamide resin and petroleum-based resin. The binder can be selected from these in consideration of the solubility in the solvent and the like. These may be used each alone or in combinations of two or more thereof.

<Oxygen Detecting Agent Sheet>

In the present embodiment, a sheet (oxygen detecting agent sheet) can be formed by using the oxygen detecting agent composition. In other words, the oxygen detecting agent sheet of the present embodiment is a sheet including the above-described oxygen detecting agent composition. Examples of an aspect of the oxygen detecting agent sheet include a sheet which includes a base material and a layer formed on the base material, the layer including the oxygen detecting agent composition.

Examples of the base material include: polyester resins such as polyethylene terephthalate; polyolefin resins such as polyethylene and polypropylene; resins such as polyacrylonitrile resin, polyvinyl chloride resin, polyvinylidene chloride resin and polyamide resin such as 6-nylon; and fibrous materials such as paper, cloth and non-woven fabric.

Examples of the method for preparing the oxygen detecting agent sheet include a method in which the above described oxygen detecting agent ink is applied to, impregnated into or printed on a sheet (sometimes referred to as "film"). The application method is not particularly limited, and heretofore known application methods can also be adopted. Examples thereof include a method using brush, spray or the like. The impregnation method is not particularly limited, and heretofore known impregnation methods can also be adopted. The printing method is not particularly limited, and heretofore known printing methods can also be adopted. Examples of the printing method include: an offset printing method, a gravure printing method, a screen printing method, a flexographic printing method and a letterpress printing method. In this case, the thickness of the oxygen detection layer is not particularly limited; however, usually, the thickness of the oxygen detection layer is preferably 0.1 to 50 μm, more preferably 1 to 30 μm and furthermore preferably 5 to 10 μm. The regulation of the thickness of the oxygen detection layer so as to fall within the above-described range allows the oxygen detection performance of the oxygen detection sheet to be more enhanced, and the exfoliation of the coating to be more effectively suppressed.

<Packaging Material for Oxygen Scavenger>

In the present embodiment, the packaging material for an oxygen scavenger may be prepared by using the oxygen detecting agent composition. The packaging material for an oxygen scavenger of the present embodiment may also be prepared by using a sheet including the above-described oxygen detecting agent composition. The packaging material for an oxygen scavenger can also be prepared by using the above-described oxygen detecting agent sheet.

<Powder-Form Oxygen Detecting Agent Composition>

The oxygen detecting agent composition of the present embodiment is also allowed to be, if necessary, a powder-form oxygen detecting agent composition by mixing, for example, the above-described support. By supporting the respective components of the oxygen detecting agent composition on the support, the handleability of the oxygen detecting agent composition can be more improved while the composition is in a powder form.

<Oxygen Detecting Agent Molded Article>

In the present embodiment, the oxygen detecting agent composition can be molded into a molded article (oxygen detecting agent molded article). Examples of the shape of the molded article include, without being limited to, a tablet obtained by compression molding the oxygen detecting agent composition. Moreover, the above-described powder-form oxygen detecting agent composition is preferably compression molded. For the compression molding, a commercially available tablet machine or the like can be used. In order to more improve the moldability, it is possible to add, if necessary, a binder such as a cellulose powder, powdery polyethylene, or starch. The shape of the molded article is not particularly limited, and heretofore known shapes can be adopted; however, among such shapes, from the viewpoint of preventing the fracture or the like of the molded article, the shape of the molded article is preferably a tablet shape such as a round shape, an oblong shape or a caplet shape. The weight per one oxygen detecting agent molded article is not particularly limited; however, the weight per one oxygen detecting agent molded article is preferably 0.05 to 5 g and more preferably 0.1 to 0.5 g. The regulation of the weight of the oxygen detecting agent molded article so as to fall within the above-described range allows the handleability and the color visibility to be more improved.

<Packaging Form>

The powder-form oxygen detecting agent composition or the oxygen detecting agent molded article is filled in a small bag formed of a transparent resin film, and thus a small bag-type oxygen indicator can be obtained. If necessary, a perforation treatment may be applied to an extent not to leak the packed substance, or a treatment aiming at control of ventilation between inside and outside the bag or the like, such as running a ventilation string through the bag, may also be applied. Even when such treatments are applied, the elution of the dye can be effectively prevented. Moreover, excellent oxygen detection performance can be sufficiently provided.

<Heat Sterilization Treatment>

The oxygen detecting agent composition of the present embodiment is placed in a packaging container together with an object to be stored such as food or an oxygen scavenger, the packaging container is hermetically sealed, and then a heat sterilization treatment such as a boil sterilization treatment at approximately 80 to 100° C., or a retort sterilization treatment (depending on the temperature region and the like, "semi-retort sterilization treatment," "retort sterilization treatment," "high-retort sterilization treatment" or the like may sometimes be properly used) at approximately 100 to 135° C. can be performed. Even when such heat sterilization treatments are applied, the elution of the dye can be suppressed. Moreover, excellent oxygen detection performance can be sufficiently provided.

EXAMPLES

Hereinafter, Examples of the present invention are presented, and the present invention is described more specifically. It is to be noted that the present invention is not intended to be limited by these Examples.

The following reagents used in following Examples were the reagents manufactured by Wako Pure Chemical Industries, Ltd.: isopropyl alcohol (hereinafter, denoted as "IPA"), ethyl acetate, methylene blue, methylene green, indigo carmine, D-glucose, maltose monohydrate, cellulose powder, magnesium hydroxide, magnesium carbonate, magnesium chloride, magnesium sulfate, lithium chloride, sodium chloride, potassium chloride, calcium chloride, sodium carbonate, sodium sulfate, sodium phosphate, trisodium citrate, and ethylene glycol.

<Experiment 1>

Example 1-1

<Preparation of Oxygen Indicator Ink>

A mixed solvent composed of 4.5 g of IPA and 4.5 g of ethyl acetate was prepared, and 1.0 g of cellulose acetate propionate (trade name "504-0.2," manufactured by Eastman Chemical Co., hereinafter denoted as "CAP") was dissolved as a binder in the mixed solvent. In the resulting solution, 0.16 g of ammonium iron blue pigment (trade name: "Milori blue FX9050," manufactured by Dainichiseika Color & Chemicals Mfg. Co., Ltd., solubility in water at 20° C.: less than 0.002 mg/100 g-$H_2O$) as a redox dye, 0.011 g of phloxine B (Food Red No. 104, manufactured by Hodogaya Chemical Co., Ltd.) as a colorant, 3.6 g of ethylene glycol as a moisturizing agent, and 2.1 g of D-glucose as a reducing agent were added and dispersed, to yield an ink A.

In a mixed solvent composed of 5.8 g of IPA and 5.8 g of ethyl acetate, 1.4 g of CAP was dissolved to prepare a solution. In the resulting solution, 10 g of magnesium hydroxide as a basic substance was mixed and dispersed to obtain a dispersion liquid.

An oxygen indicator ink was obtained by mixing 1.1 g of the ink A, 1.1 g of the dispersion liquid, 0.7 g of IPA and 0.7 g of ethyl acetate.

<Preparation of Oxygen Detecting Agent Sheet>

The ink was applied to the surface of a sheet of a synthetic paper (polypropylene-based sheet, trade name: "FPD-80," manufactured by Yupo Corp.) cut to 100 mm×150 mm according to the following procedure. The application of the ink was performed by using a bar coater (manufactured by Tester Sangyo Co., Ltd.). First, as a protective layer, a medium (trade name: "CLIOS Medium (A)," manufactured by DIC Graphics Corp.) was applied and dried by blowing hot air at 60° C. Next, the oxygen indicator ink was applied onto the protective layer and dried by blowing hot air at 60° C. for 10 seconds to form an oxygen detection layer. Finally, the medium (trade name: "CLIOS Medium (A)") was applied onto the surface of the oxygen detection layer, and dried by blowing hot air at 60° C. for 10 seconds to obtain an oxygen detecting agent sheet (polypropylene-based sheet/protective layer 1/oxygen detection layer/protective layer 2).

A laminated film composed of a biaxially stretched polypropylene film (thickness: 20 μm) and an unstretched polypropylene film (thickness: 30 μm) was prepared. By using this laminated film, there was prepared a three-side sealed bag of 25 mm in the longitudinal direction×25 mm in the transverse direction such that the unstretched polypropylene film was arranged inside the bag.

The obtained oxygen detecting agent sheet was cut to a size of 5 mm in the longitudinal direction×15 mm in the transverse direction, to prepare an oxygen detecting agent sheet piece. The oxygen detecting agent sheet piece was placed in the three-side sealed bag in such a way that the protective layer 2 of the oxygen detecting agent sheet piece was brought into contact with the inside surface (the unstretched polypropylene film side) of the three-side sealed bag, and then the three-side sealed bag was heat sealed to prepare an evaluation sample.

<Evaluation of Resistance to Heat Sterilization Treatment and Evaluation of Oxygen Detection Performance>

In an oxygen barrier bag, an evaluation sample (the three-side sealed bag), an oxygen scavenger (trade name: "Ageless SA-500," manufactured by Mitsubishi Gas Chemical Company, Inc., oxygen scavenger composition: 10 g) and 500 mL of air were enclosed, and then the bag was hermetically sealed to obtain a hermetically sealed body. By using the hermetically sealed body, the evaluation of the resistance to heat sterilization treatment and the evaluation of the oxygen detection performance were performed.

(Evaluation of Resistance to Heat Sterilization Treatment)

The obtained hermetically sealed body was subjected to a retort treatment at 121° C. for 30 minutes, and the resistance to the heat sterilization treatment was evaluated by identifying the presence or absence of the contamination immediately after the retort treatment. It is to be noted that the oxygen concentration in the hermetically sealed body immediately after being subjected to the retort treatment was verified to be less than 0.1% by volume by using a gas chromatograph ("GC-14A," manufactured by Shimadzu Corp.). The presence or absence of the contamination immediately after being subjected to the retort treatment was evaluated on the basis of the following standards.

"○": No coloration of blue color due to the dye was found, and the evaluation sample (the three-side sealed bag) maintained the colorless state.

"X": By coloration of blue color due to the dye, the evaluation sample (the three-side sealed bag) was changed in color to blue (insufficient resistance to heat sterilization treatment).

(Evaluation of Oxygen Detection Performance)

The obtained hermetically sealed body was subjected to a retort treatment at 121° C. for 30 minutes, and then the oxygen barrier bag was opened and the oxygen detection sheet was taken out. The oxygen detection sheet was allowed to stand still in an air atmosphere at 25° C., and the oxygen detection performance was evaluated by visually identifying the change of the color after an elapsed time of 6 hours and the change of the color after an elapsed time of 24 hours. The oxygen detection performance was evaluated on the basis of the following standards.

"⊚": At the point of the standing still time of 6 hours, the color of the oxygen detection sheet changed to blue (the color indicating that the oxygen concentration of 0.5% by volume or more).

"◯": At the point of the standing still time of 6 hours, the color of the oxygen detection sheet before the opening of the oxygen barrier bag did not change to blue (for example, the color was pink), and at the point of the standing still time of 24 hours, the color of the oxygen detection sheet changed to blue.

"X": Even at the point of the standing still time of 24 hours, the color of the oxygen detection sheet did not change to blue (insufficient oxygen detection performance).

The results thus obtained are shown in Table 1.

Example 1-2

The experiment was performed in the same manner as in Example 1-1 except that iron hexacyanoferrate (manufactured by Santa Cruz Biotechnology, Inc., the solubility in water at 20° C.: less than 0.002 mg/100 g-$H_2O$) was used in place of ammonium iron blue pigment. The results thus obtained are shown in Table 1.

Comparative Example 1-1

The experiment was performed in the same manner as in Example 1-1 except that 0.019 g of methylene blue (the solubility in water at 20° C.: 5000 mg/100 g-$H_2O$) was used in place of ammonium iron blue pigment. The results thus obtained are shown in Table 1.

TABLE 1

| | Redox dye | Solubility in water of redox dye (25° C.) [mg/100 g-$H_2O$] | Evaluation of resistance to heat sterilization treatment | Evaluation of oxygen detection performance |
|---|---|---|---|---|
| Example 1-1 | Ammonium iron blue pigment | <0.002 | ◯ | ◯ |
| Example 1-2 | Iron hexacyanoferrate | <0.002 | ◯ | ◯ |
| Comparative Example 1-1 | Methylene blue | 5000 | X | ◯ |

As can be seen from Table 1, for example, it has been verified at least that in each of Examples 1-1 and 1-2, the evaluation of the resistance to heat sterilization treatment and the evaluation of the oxygen detection performance were both satisfactory. On the other hand, it has been verified that in Comparative Example 1-1, the evaluation of the resistance to heat sterilization treatment was poor.

Example 1-3

<Preparation of Tablet-Shaped Oxygen Detecting Agent>

A powder-form oxygen detecting agent composition was obtained by mixing, with an automatic mortar, 100 g of magnesium carbonate, 2.0 g of cellulose powder, 0.50 g of ammonium iron blue pigment, 0.05 g of phloxine B (Food Red No. 104, manufactured by Hodogaya Chemical Co., Ltd.), 5.0 g of maltose monohydrate, 5.0 g of magnesium sulfate, and 5.0 g of water. By using a pressure molding machine (small-scale tablet machine "VELA 5," manufactured by Kikusui Seisakusho Ltd.), a pressure of 10 kN was applied for 5 seconds to the powder-form oxygen detecting agent composition to obtain a tablet-shaped oxygen detecting agent of 3.2 mm in thickness and 7 mmϕ in diameter.

<Evaluation of Resistance to Heat Sterilization Treatment>

A laminated film composed of a biaxially stretched polypropylene film (thickness: 20 μm) and an unstretched polypropylene film (thickness: 30 μm) was prepared. By using this laminated film, there was prepared a three-side sealed bag of 25 mm in the longitudinal direction×25 mm in the transverse direction such that the unstretched polypropylene film was arranged inside the bag. One tablet of the obtained tablet-shaped oxygen detecting agent was placed in the three-side sealed bag, and the opening of the three-side sealed bag was heat sealed to prepare an evaluation sample.

<Evaluation of Resistance to Heat Sterilization Treatment and Evaluation of Oxygen Detection Performance>

In an oxygen barrier bag, an evaluation sample (the three-side sealed bag), an oxygen scavenger (trade name: "Ageless SA-500," manufactured by Mitsubishi Gas Chemical Company, Inc., oxygen scavenger composition: 10 g) and 200 mL of air were enclosed, and then the bag was hermetically sealed to obtain a hermetically sealed body. The obtained hermetically sealed body was subjected to a retort treatment at 121° C. for 30 minutes, and the evaluation of the resistance to heat sterilization treatment and the evaluation of the oxygen detection performance were performed in the same manner as in Example 1-1. The results thus obtained are shown in Table 2.

Example 1-4

The experiment was performed in the same manner as in Example 1-3 except that D-glucose was used in place of maltose monohydrate. The results thus obtained are shown in Table 2.

Comparative Examples 1-2 and 1-3

In each of Comparative Examples 1-2 and 1-3, the experiment was performed in the same manner as in Example 1-4 except that 0.05 g of the redox dye shown in Table 2 was used in place of 0.50 g of ammonium iron blue pigment. The results thus obtained are shown in Table 2.

TABLE 2

| | Redox dye | Solubility in water of redox dye (25° C.) [mg/100 g-H₂O] | Reducing agent | Evaluation of resistance to heat sterilization treatment | Evaluation of oxygen detection performance |
|---|---|---|---|---|---|
| Example 1-3 | Ammonium iron blue pigment | <0.002 | Maltose monohydrate | ○ | ○ |
| Example 1-4 | Ammonium iron blue pigment | <0.002 | D-Glucose | ○ | ○ |
| Comparative Example 1-2 | Methylene blue | 5000 | Maltose monohydrate | X | ○ |
| Comparative Example 1-3 | Indigo carmine | 1000 | D-glucose | ○ | X |

As can be seen from Table 2, for example, it has been verified at least that in each of Examples 1-3 and 1-4, the evaluation of the resistance to heat sterilization treatment and the evaluation of the oxygen detection performance were both satisfactory. On the other hand, it has been verified that in each of Comparative Examples 1-2 and 1-3, at least either of the evaluation of the resistance to heat sterilization treatment and the evaluation of the oxygen detection performance was poor. It is considered that in Comparative Example 1-2 using methylene blue which is an organic substance, the dye was eluted due to the heat sterilization treatment to cause contamination. It is considered that in Comparative Example 1-3 using indigo carmine, the dye was thermally decomposed during the heat sterilization treatment, and consequently the oxygen detection performance was insufficient.

<Experiment 2>

Example 2-1

<Preparation of Tablet-Shaped Oxygen Detecting Agent>

A powder-form oxygen detecting agent composition was obtained by mixing, with an automatic mortar, 100 g of magnesium carbonate, 2.0 g of cellulose powder, 0.50 g of ammonium iron blue pigment (trade name: "Milori blue FX9050," manufactured by Dainichiseika Color & Chemicals Mfg. Co., Ltd.), 0.05 g of phloxine B (Food Red No. 104, manufactured by Hodogaya Chemical Co., Ltd.), 5.0 g of maltose monohydrate, 0.50 g of sodium chloride, and 5.0 g of water. By using a pressure molding machine, a pressure of 10 kN was applied for 5 seconds to the powder-form oxygen detecting agent composition to obtain a tablet-shaped oxygen detecting agent of 3.2 mm in thickness and 7 mmφ in diameter.

<Preparation of Small Bag-Type Oxygen Indicator>

A laminated film composed of a biaxially stretched polypropylene film (thickness: 20 μm) and an unstretched polypropylene film (thickness: 30 μm) was prepared. By using this laminated film, there was prepared a three-side sealed bag of 25 mm in the longitudinal direction×25 mm in the transverse direction such that the unstretched polypropylene film was arranged inside the bag.

One tablet of the obtained tablet-shaped oxygen detecting agent was placed in the three-side sealed bag, and the opening of the three-side sealed bag was heat sealed. In the three-side sealed bag, a hole of 0.5 mm in diameter was formed at a position so as to pass through between the inside and outside of the bag, and thus a small bag-type oxygen indicator was obtained and used as an evaluation sample.

<Evaluation of Resistance to Heat Sterilization Treatment and Evaluation of Oxygen Detection Performance>

In an oxygen barrier bag, an evaluation sample (the small bag-type oxygen indicator), an oxygen scavenger (trade name: "Ageless SA-500," manufactured by Mitsubishi Gas Chemical Company, Inc., oxygen scavenger composition: 10 g) and 200 mL of air were enclosed, and then the bag was hermetically sealed to obtain a hermetically sealed body. The obtained hermetically sealed body was subjected to a retort treatment at 121° C. for 30 minutes, and the evaluation of the resistance to heat sterilization treatment and the evaluation of the oxygen detection performance were performed in the same manner as in Example 1-1. The results thus obtained are shown in Table 3.

Examples 2-2 to 2-5

In each of Examples 2-2 to 2-5, the experiment was performed in the same manner as in Example 2-1 except that the sodium salt (0.50 g) shown in Table 3 was used in place of sodium chloride. The results thus obtained are shown in Table 3.

Example 2-6

The experiment was performed in the same manner as in Example 2-1 except that sodium chloride was not mixed. The results thus obtained are shown in Table 3.

Examples 2-7 to 2-10

In each of Examples 2-7 to 2-10, the experiment was performed in the same manner as in Example 2-1 except that the metal salt (0.50 g) shown in Table 3 was used in place of sodium chloride. The results thus obtained are shown in Table 3.

TABLE 3

| | Metal salt | Evaluation of resistance to heat sterilization treatment | Evaluation of oxygen detection performance |
|---|---|---|---|
| Example 2-1 | NaCl | ○ | ◎ |
| Example 2-2 | Na₂SO₄ | ○ | ◎ |
| Example 2-3 | Na₂CO₃ | ○ | ◎ |
| Example 2-4 | Na₃PO₄ | ○ | ◎ |
| Example 2-5 | Trisodium citrate | ○ | ◎ |
| Example 2-6 | None | ○ | ○ |

TABLE 3-continued

| | Metal salt | Evaluation of resistance to heat sterilization treatment | Evaluation of oxygen detection performance |
|---|---|---|---|
| Example 2-7 | LiCl | ○ | ○ |
| Example 2-8 | KCl | ○ | ○ |
| Example 2-9 | MgCl$_2$ | ○ | ○ |
| Example 2-10 | CaCl$_2$ | ○ | ○ |

Examples 2-11 to 2-13

In each of Examples 2-11 to 2-13, the experiment was performed in the same manner as in Example 2-5 except the addition amount of trisodium citrate was altered to the addition amount listed in Table 4. The results thus obtained are shown in Table 4. It is to be noted that the "sodium/redox dye (mass ratio)" in Table 4 is the ratio of sodium (sodium salt and sodium ion) to the redox dye on the basis of the mass of the sodium atom. For example, the "sodium/redox dye (mass ratio)" in Example 2-11 is {0.2 g×(22.99×3/258.06)}/{0.5 g}=0.1.

TABLE 4

| | Addition amount of trisodium citrate [g] | Sodium/redox dye (mass ratio) | Evaluation of resistance to heat sterilization treatment | Evaluation of oxygen detection performance |
|---|---|---|---|---|
| Example 2-5 | 0.5 | 0.3 | ○ | ◎ |
| Example 2-11 | 0.2 | 0.1 | ○ | ◎ |
| Example 2-12 | 1 | 0.5 | ○ | ◎ |
| Example 2-13 | 2 | 1.1 | ○ | ◎ |

As can be seen from Tables 3 and 4, for example, it has been verified at least that the inclusion of a sodium salt (or sodium ion) allows more excellent oxygen detection performance to be provided.

Example 2-14

A tablet-shaped oxygen detecting agent was prepared in the same manner as in Example 2-5 except that iron hexacyanoferrate (manufactured by Santa Cruz Biotechnology, Inc.) was used in place of ammonium iron blue pigment. Then, by using the obtained tablet-shaped oxygen detecting agent, the evaluation of the resistance to heat sterilization treatment and the evaluation of the oxygen detection performance were performed in the same manner as in Example 2-5. Consequently, the evaluation of the resistance to heat sterilization treatment was "○" and the evaluation of the oxygen detection performance was "◎."

The present application is based on the Japanese Patent Application No. 2013-209349 filed on Oct. 4, 2013 at the Japan Patent Office, and the Japanese Patent Application No. 2014-011244 filed on Jan. 24, 2014 at the Japan Patent Office, and the contents of these are incorporated herein by reference.

INDUSTRIAL APPLICABILITY

According to the present invention, an oxygen detecting agent composition, which can at least suppress the elution of a redox dye, is provided. In particular, there is provided an oxygen detecting agent composition capable of suppressing the elution of the redox dye even when the oxygen detecting agent composition is subjected to a heat sterilization treatment such as a boil treatment or a retort treatment. Accordingly, the detection of pin holes before and after the heat sterilization treatment is facilitated, the labor saving in the detection and exclusion of defective products is enabled, and the oxygen detecting agent composition can be effectively used in, for example, the management of the storage state of various articles such as food and pharmaceuticals.

The invention claimed is:

1. An oxygen detecting agent composition comprising:
a redox dye, a reducing agent and an inorganic salt comprising sodium, wherein the redox dye comprises a compound represented by general formula (1):

$$A_xMA[MB(CN)_6]_y \cdot zH_2O \tag{1}$$

wherein A represents a cation; MA represents a metal atom(s) of one or more types of metals selected from the group consisting of vanadium, chromium, manganese, iron, ruthenium, cobalt, rhodium, nickel, palladium, platinum, copper, silver, zinc, lanthanum, europium, gadolinium, lutetium, barium, strontium and calcium; MB represents a metal atom(s) of one or more types of metals selected from the group consisting of vanadium, chromium, molybdenum, tungsten, manganese, iron, ruthenium, cobalt, nickel, platinum and copper; x is a number of 0 to 3, y is a number of 0.3 to 1.5; and z is a number of 0 to 30,
and the reducing agent comprises at least one member selected from monosaccharides; disaccharides; ascorbic acid and the salts thereof; dithionous acid and the salts thereof; and cysteine and the salts thereof.

2. The oxygen detecting agent composition according to claim 1, wherein the redox dye is an iron blue pigment.

3. The oxygen detecting agent composition according to claim 1, further comprising a basic substance.

4. The oxygen detecting agent composition according to claim 1, further comprising a support.

5. A molded article comprising the oxygen detecting agent composition according to claim 1.

6. A sheet comprising the oxygen detecting agent composition according to claim 1.

7. A packaging material for an oxygen scavenger, comprising the molded article according to claim 5.

8. An oxygen scavenger comprising an oxygen scavenger composition, and the packaging material for an oxygen scavenger according to claim 6 which packages the oxygen scavenger composition.

9. A packaging material for an oxygen scavenger, comprising the sheet according to claim 6.

* * * * *